United States Patent [19]
Cook et al.

[11] 3,953,429
[45] Apr. 27, 1976

[54] ANAESTHETIC STEROIDS OF THE ANDROSTANCE AND PREGNANE SERIES

[75] Inventors: Martin Christopher Cook, Chalfont St. Peter; Robin Lawrence, London; Gordon Hanley Phillipps, Wembley; Anne Christine Hunter, Ruislip; Christopher Earle Newall, London; Leslie Stephenson, London; Niall Galbraith Weir, London, all of England

[73] Assignee: Glaxo Laboratories Limited, Greenford, England

[22] Filed: Feb. 19, 1974

[21] Appl. No.: 443,451

Related U.S. Application Data

[63] Continuation of Ser. No. 208,959, Dec. 16, 1971, abandoned.

[30] Foreign Application Priority Data

Dec. 17, 1970 United Kingdom............... 60064/70

[52] U.S. Cl............... 260/239.55 R; 260/239.55 C; 260/397.1; 260/397.4; 260/397.45; 424/243
[51] Int. Cl.$^2$.......................................... C07J 5/00
[58] Field of Search........ 260/397.4, 397.45, 239.55

[56] References Cited
UNITED STATES PATENTS
3,048,606   8/1962   Wettstein et al............... 260/397.45

OTHER PUBLICATIONS

Cocker et al., "Journ. of Med. Chemistry" (1965), pp. 417–425.
Atkinson et al., "Jour. of Med. Chemistry" (1965), Vol. 8, pp. 426–432.

*Primary Examiner*—Elbert L. Roberts
*Attorney, Agent, or Firm*—Bacon & Thomas

[57] ABSTRACT

Steroids of the androstane and pregnane series possessing a 2α-hydrogen or halogen or an alkyl group; a 3α-hydroxy or acyloxy group, a 3β-hydrogen or alkyl group; an 11β-hydrogen or hydroxy group or an epoxy group linked also to the 9-position; an 11α-hydrogen or alkyl or allyl group; or an 11-oxo group; a 16 hydrogen or halogen or a methyl or dimethyl group; a 20-oxo or ethylenedioxy group; and a 20-methyl or alkoxy group. The compounds may be unsaturated at the 1(2), 8(9) or 9(11) positions.

The compounds possess anaesthetic properties.

14 Claims, No Drawings

ANAESTHETIC STEROIDS OF THE ANDROSTANCE AND PREGNANE SERIES

This is a continuation of application Ser. No. 208,959, filed Dec. 16, 1971, now abandoned.

This invention is concerned with improvements in or relating to compounds of the pregnane and androstane series having useful anaesthetic activity.

It has long been known that a number of steroids give rise to profound depression of the central nervous system and act pharmacodynamically as anaesthetics or hypnotics. Such compounds have been the subject of considerable study in any attempt to find anaesthetics to replace such substances as thiopentone sodium normally used but well known to be accompanied by some degree of hazard and disadvantage. The literature shows that very many steroid compounds have been studied in this regard. Reviews and discussions of some of the work carried out are to be found, for example, in "Methods in Hormone Research" (Edited by Ralph I. Dorfman, Vol. III Part A, Academic Press, London and New York, 1964, pages 415–475); H. Witzel, Z. Vitamin Hormon-Fermentforsch 1959, 10, 46–74; H. Selye, Endocrinology, 1942, 30, 437–453; S. K. Figdor et al., J. Pharmacol. Exptl. Therap., 1957, 119, 299–309 and Atkinson et al., J. Med. Chem. 1965, 8, 426–432.

A thorough review of the literature indicates that anaesthetic steroids generally possess poor activity and/or long induction periods. With such compounds a variety of undesired side effects such as paraesthesia and vein damage have been noted. Steroids possessing anaesthetic activity hitherto described are generally relatively simple pregnane derivatives, often hydroxylated in the 3-position, the general trend having been in the latter case to study 3β-hydroxy compounds rather than 3α-hydroxy compounds.

We have now found that certain 3α-oxygenated steroids of the pregnane and androstane series which are more particularly defined hereinafter possess remarkable anaesthetic properties and thus may comprise the active component of pharmaceutical compositions for inducing anaesthesia or, in suitable doses, sedation or tranquillisation. By the term 'pharmaceutical' as used herein we intend reference to both human and veterinary medicine.

According to the present invention there are provided pharmaceutical compositions containing one or more compounds of the general formula:

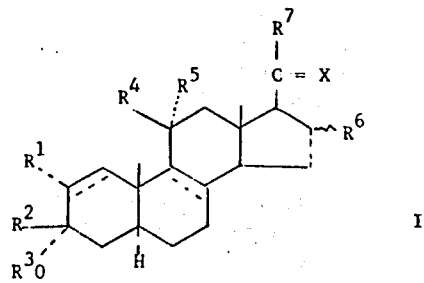

I where
$R^1$ is hydrogen or an alkyl, preferably a lower alkyl group (e.g. a methyl group), or a halogen atom (e.g. chlorine or bromine);

$R^2$ is hydrogen or an alkyl group, preferably a lower alkyl group e.g. a methyl, ethyl or pentyl group;

$R^3$ is hydrogen or lower acyl (e.g. acetyl, trichloroacetyl or trifluoroacetyl);

$R^4$ is hydrogen, hydroxy or an epoxy group or carbon-carbon bond linked also to the 9-position;

$R^5$ is hydrogen (when $R^4$ is an epoxy group or carbon-carbon bond linked to the 9-position) or is hydrogen or hydroxy (when $R^4$ is hydrogen) or is lower alkyl e.g. methyl, or allyl (when $R^4$ is hydroxy), or $R^4$ and $R^5$ together represent an oxo group;

$R^6$ is hydrogen, methyl, gem-dimethyl or halogen (e.g. chlorine), $R^7$ is a methyl group or a lower alkoxy group (e.g. methoxy group);

X is O or, when $R^7$ is a methyl group, ethylenedioxy; the dotted line at the 1(2) and 8(9) positions indicating an optional double bond at one or more of these positions, provided that at least one of $R^1$, $R^2$, $R^3$ and $R^6$ is other than hydrogen when X and $R^4$ and $R^5$ represent oxo groups or $R^4$ and $R^5$ are both hydrogen, and the 1(2) and 8(9) bonds are saturated)

together with a pharmaceutical carrier or excipient;

The term "lower" as used herein with reference to alkyl and alkoxy groups indicates that the group in question contains 1–6 carbon atoms. As applied to acyl groups it indicates that the acyl group contains 2–6 carbon atoms.

Compounds of the foregoing general formula are excellent anaesthetics and have been found to induce anaesthesia with generally short induction periods, the anaesthetic action at suitable doses being in general instantaneous; the compounds are thus excellent anaesthetics for inducing anaesthesia which is to be maintained e.g. by an inhalation anaesthetic such as ether, halothane, nitrous oxide, trichloroethylene etc. The compounds are however capable of maintaining anaesthesia and analgesia to a sufficient degree to enable various surgical operations to be conducted without the aid of an inhalation anaesthetic, the required degree of anaesthesia being maintained if necessary by repeated administration (or even continuous administration). Moreover, the said anaesthetics in accordance with the invention in general give rise to minimal side-effects compared with previously described steroidal anaesthetics.

The compounds of formula I as defined above are new, provided that $R^5$ is hydrogen when $R^4$ is hydrogen or an epoxy group or a carbon-carbon bond linked to the 9-position, and that at least one of $R^1$, $R^2$, and $R^6$ is other than hydrogen when $R^4$ and $R^5$ are both hydrogen atoms or are an oxo group and the 1(2) and 8(9) bonds are saturated. Such new compounds constitute a further feature of the invention.

An important class of compounds of formula I is that possessing $\Delta^1$ unsaturation especially those wherein $R^4$ and $R^5$ are hydrogen or together represent an oxo group.

Other important classes of compounds according to the invention are those possessing a 2α substituent and/or unsaturation at the 8(9) position, particularly when there is an oxo group at the 11 position (i.e. when $R^4$ and $R^5$ together represent an oxo group).

Other substituents may of course be present in the just-mentioned important classes, particularly substituents at the 16 position as defined above.

Particularly preferred compounds for use in the compositions according to the invention are:

3α-hydroxy-16β-methyl-5α-pregnane-11,20-dione;
20,20-ethylenedioxy-3α-hydroxy-5α-pregnan-11-one;
3α-trichloroacetoxy-5α-pregnane-11,20-dione;
3α-trifluoroacetoxy-5α-pregnane-11,20-dione;
16α-chloro-3α-hydroxy-5α-pregnane-11,20-dione;
3α,11α-dihydroxy-5α-pregnan-20-one;
3α,11β-dihydroxy-11α-methyl-5α-pregnan-20-one;
9β,11β-epoxy-3α-hydroxy-5α-pregnan-20-one;
3α-hydroxy-3β-methyl-5α-pregnane-11,20-dione;
3α-hydroxy-2α-methyl-5α-pregnane-11,20-dione;
3α-hydroxy-5α-pregn-8-ene-11,20-dione;
3α-hydroxy-17β-methoxycarbonyl-5α-androst-1-ene;
3α-hydroxy-5α-pregn-1-ene-11,20-dione;
3α-hydroxy-5α-pregn-1-en-20-one;
3α-hydroxy-16α-methyl-5α-pregnane-11,20-dione.

Many of the above-described steroidal anaesthetic compounds are poorly soluble in water. We have found however that they may be formulated for parenteral administration in an aqueous solution of a parenterally acceptable non-ionic surface active agent.

The non-ionic surface active agents used for the purpose of this invention are generally those of the water soluble type, conveniently having an HLB value of at least 9, preferably at least about 12, advantageously at least about 13. Preferably the HLB value of the surface active agent is not greater than about 15 although it may, for example, be as high as 18. The surface active agent must naturally be one which is physiologically compatible, i.e. of itself give rise to no physiologically unacceptable side effects in the dosages employed in the intended species to be treated (man or animal). Surface active agents for use in accordance with the invention are for example to found among the following non-ionic surfactants and classes of surfactants: Polyoxyethylated derivatives of fatty (C12–C20) glyceride oils, e.g. castor oil, containing from 35 to 45 or even up to 60 oxyethylene groups, per mole of fatty oil. Polyoxyethylene ethers (containing from 10 to 30 oxyethylene groups) of long chain alcohols (containing for example from 12–18 carbon atoms).

Polyoxyethylene-polyoxypropylene ethers containing from 15 to 35 and from 15 to 30 oxyethylene and oxypropylene groups respectively. Polyoxyethylene ethers (containing from 6 to 12 oxyethylene groups) of alkyl phenols the alkyl groups of which preferably contain 6 – 10 carbon atoms.

Polyoxyethylated (containing from 15 to 30 oxyethylene groups) fatty acid (e.g. C12–18) esters of sugar alcohol anhydrides e.g. sorbitan or mannitan. Long-chain (e.g. C10–16) alkanoyl mono- and di-alkanolamides (the alkanol portions of which for example contain 1–5 C atoms) for example lauroyl mono- and di-ethanolamides. Polyethylene glycol esters (containing from 6 to 40 ethylene oxide units) of long chain fatty acids (containing for example 12–18 C atoms) e.g. polyethyleneglycol mono-oleate (containing for example 8 ethylene oxide units).

Examples of non-ionic surface active agents, of the foregoing types, useful in accordance with the invention includes:

Cremophor EL, a polyoxyethylated castor oil containing about 40 ethylene oxide units per triglyceride unit;

Tween 80, polyoxyethylene sorbitan monooleate contaning about 20 ethylene oxide units;

Tween 60, polyoxyethylene sorbitan monostearate containing about 20 ethylene oxide units; and Tween 40, polyoxyethylene sorbitan monopalmitate containing about 20 ethylene oxide units.

The expression "solutions" is used herein to denote liquids which have the appearance of true solutions and are thus optically clear and capable of passage, for example, through a micro-porous filter, irrespective of whether such solutions are true solutions in the classical chemical sense and irrespective of whether they are stable or metastable. Thus it may be that the steroid is associated with micelles. The solutions of this invention, irrespective of their precise physical nature, behave as true solutions for the practical purpose of intravenous injections.

The proportion of surface active agent to be used in the compositions of this invention depends upon its nature and upon the concentration of steroid desired in the final composition.

In preferred compositions according to the invention the proportion of surfactant is preferably at least 5% by weight and advantageously about 10% by weight. A very convenient proportion of surfactant has been found to be 20% by weight but 30% and up to 50% may be used. The proportions of surfactant are expressed by weight in relation to the total volume of the composition in metric units.

As will be clear, the proportion of steroid in the aqueous solution according to the invention depends upon the nature and amount of surface active agent used. The composition will contain at least 1 mg/ml of steroid and solutions can be made containing for example up to 10 mg/ml.

In all cases, the relative proportion of the various components are adjusted to give a clear solution.

In a preferred method of preparing the solutions according to the invention the steroid is first dissolved in the selected surfactant for example, with heating and the resulting solution dissolved in water. Alternatively the steroid may be dissolved in a volatile organic solvent advantageously having a boiling point of less than about 80°C which is miscible with the surface active agent such as a volatile lower aliphatic ketone e.g. acetone or methyl ethyl ketone or a volatile halogenated hydrocarbon e.g. chloroform or methylene chloride. Acetone is particularly preferred for this purpose. The surface active agent is then added to this solution, the organic solvent removed by evaporation, for example by passing a stream of an inert gas through the solution e.g. nitrogen and the resulting solution of steroid in surfactant is mixed with water.

The solutions may also be prepared by shaking the steroid with an aqueous solution of the surface active agent.

In all cases simple tests enable one to determine the relative proportions of surface active agent required.

The anaesthetic solutions according to the invention are generally administered by intravenous injection although as is known in the anaesthetic art in certain cases, e.g. with young children, intramuscular injection might be preferred.

As is usual in the case of anaesthetics, the quantity of steroid used to induce anaesthesia depends upon the weight of the individual to be anaesthetised. For intravenous administration in the average man a dose of from 0.5 to 30 mg/Kg will in general be found to be satisfactory to induce anaesthesia, the preferred dose being within the range of from 0.7 to 20 mg/Kg. The dose will naturally vary to some extend dependent upon the physical condition of the patient, and the degree and period of anaesthesia required, all as is well known in the art. It is thus possible by adjustment of the dose to achieve durations of anaesthesia varying from about 10 minutes to up to an hour or more. If it is desired to maintain prolonged anaesthesia, repeated doses of the solutions of this invention may be used, such repeated doses being generally either of the same order or lower than the original dose. Alternatively continuous administration may be undertaken at for example a rate of 0.09–1.4 mg/kg/min.

Where the anaesthetic solutions are administered intramuscularly, higher doses are generally necessary.

It will be appreciated that most of the compounds of general formula I above are substitution derivatives and/or analogues of 3α-hydroxy-5α-pregnan-20-one and may be prepared by conventional methods.

We now describe by way of example only general methods for the introduction into an appropriate steroid molecule of the substituents $R^1$, $R^2$, $R^3$, $R^4$, $R^5$, $R^6$, $R^7$ and X as well as unsaturation at 1(2), 8 and 9(11).

The compounds according to the invention may be prepared by any convenient method, e.g. as described in "Steroid Reactions" Djerassi, published in 1963 by Holden-Day, Inc, San Francisco.

Compounds of formula I wherein $R^3$ represents an acyl group may be prepared by known methods, for example by reacting a compound of formula I wherein $R^3$ represents a hydrogen atom with an acylating agent. The acylation is preferably effected under basic conditions conveniently using a tertiary amine (e.g. pyridine, collidine or trimethylamine) as the base. The reaction is conveniently effected in an organic solvent, for example a halogenated hydrocarbon e.g. methylene chloride or an etheric solvent e.g. tetrahydrofuran or the tertiary amine used as the base. The anhydride or halide, i.e. the chloride or bromide, of the desired acid is preferably used as the acylating agent.

Compounds of formula I wherein X represents an ethylenedioxy group may be prepared, for example, by reaction of a corresponding 20-oxo pregnane of formula I with ethylene glycol preferably in the presence of an acid catalyst, for example an aryl sulphonic acid e.g. toluene p-sulphonic acid. The reaction is conveniently effected using ethylene glycol as solvent, preferably at an elevated temperature, for example under reflux. Methods of ketalisation are described in "Steroid Reactions" on pages 2–22.

The compounds of formula I wherein $R^5$ represents a hydroxy group and $R^4$ represents a hydrogen atom may be prepared for example by the stereospecific reduction of a compound of formula I wherein $R^4$ and $R^5$ together represent an oxygen atom and preferably X represents an ethylenedioxy group.

This is preferably effected using an alkali metal, advantageously lithium, or an alkaline earth metal, advantageously calcium, and a suitable nitrogen base e.g. ammonia or a lower alkylamine, advantageously ethylamine as reducing agent. The reaction is conveniently effected in a solvent, preferably comprising the nitrogen base used in the reducing agent.

Compounds of formula I wherein $R^5$ represents a lower alkyl or allyl group and $R^4$ represents a hydroxy group and X represents an oxygen atom may be prepared, for example, from the corresponding compound of formula I wherein $R^4$ and $R^5$ together represent an oxygen atom and, where $R^7$ represents a methyl group, X represents an ethylenedioxy group, by reaction with an alkylating or allylating agent, preferably an alkali metal alkyl or allyl compound, advantageously methyl lithium or allyl lithium. The alkylation or allylation may conveniently be effected in an aprotic organic solvent for example an etheric solvent such as diethyl ether and/or tetrahydrofuran, preferably at a temperature of 0°–100°C, e.g. 15°–65°C.

Compounds of formula I and precursors therefor wherein X represents an ethylenedioxy group thus produced may, if desired, be converted into compounds of formula I wherein X represents an oxygen atom by known methods for example by hydrolysis in the presence of an inorganic or organic acid such as a hydrohalic acid e.g. hydrochloric acid or a lower alkanoic acid e.g. acetic acid. The hydrolysis may conveniently be effected at a temperature of 0°–100°C.

The preparation of compounds of formula I wherein $R^6$ represents a 16β-methyl group may be effected for example by hydrogenation of a $\Delta^{16}$-analogue thereof preferably using catalytically activated hydrogen. Suitable catalysts include, for example platinum metal catalysts, preferably a palladium catalyst e.g. palladium on charcoal. The hydrogenation is preferably effected in a organic solvent, for example a lower alkanol e.g. methanol or ethanol, an etheric solvent e.g. tetrahydrofuran or diethyl ether, a halogenated hydrocarbon e.g. methylene chloride or a lower alkanoic acid ester e.g. ethyl acetate.

The 16-methyl-16-ene-analogues of steroids of formula I may be prepared by known methods, for example by the method of Negata et al (Helv. Chim. Acta 1959, 42, 1399) from the corresponding 3β-hydroxy-16-methyl-16-ene-steroid. This technique can be used generally for converting a 3β-hydroxy analogue into a compound of formula I. The 3β-hydroxy compound may thus be converted into a hydrocarbonsulphonyloxy derivative thereof, preferably the 3β-toluene-sulphonyloxy derivative, which may then, for example, be reacted with a salt of a lower alkanoate e.g. triethylammonium acetate, to give the 3α-acyloxy compound. The 3α-acyloxy compound may be subsequently hydrolysed to give the 3α-hydroxy compound.

20-Oxo compounds of formula I having a 16α-methyl substituent can be obtained from corresponding 16-unsubstituted $\Delta^{16}$-20-oxo compounds by reaction with a metal methyl derivative such as lithium dimethyl cuprate or, using a copper catalyst, a methyl magnesium halide, e.g. bromide or iodide. The reaction is preferably effected in an ether solvent e.g. diethyl ether.

Compounds of formula I wherein $R^4$ represents an epoxy group linked also at the 9β-position may be prepared by known methods. It has been found convenient to prepare such compounds from the corresponding 9α-halo-11β-hydroxy compound by elimination of hydrogen halide e.g. HBr. The elimination is preferably effected under alkaline conditions, for example using an aqueous solution of an alkali metal hydroxide e.g. sodium hydroxide, advantageously at a pH of 11 to 12.5. The reaction may be effected at about ambient temperature e.g. for a period of about 15 minutes. The 9α-halo-11β-hydroxy steroids used in this reaction, preferably the 9α-bromo-compounds, may be prepared by known methods, for example from the corresponding 9,11-dehydro-compounds by reaction with a source of hypohalous acid. Suitable sources of hypohalous acid include, for example aqueous acidic solutions of halogenating agents e.g. N-bromosuccinimide.

The 9,11-dehydro steroids of formula I may be prepared by known methods, e.g. by hydrogenation of the corresponding 9(11),16-diene which may be prepared, for example, by a method analogous to that set forth hereinbefore for the preparation of 16-methyl-$\Delta^{16}$-compounds used in the preparation of 16$\beta$-methyl compounds according to the invention and as described in our Belgian Pat. No. 752165 from the corresponding 3$\beta$-hydroxy-9(11),16-diene compounds.

Compounds according to the invention having a double bond between the 8- and 9-positions and an 11-oxo group may be prepared, for example by dehydrohalogenation of a corresponding 9$\alpha$-halo-11-oxo-compound. The dehydrohalogenation may, in general, be effected under generally mild conditions, for example using a nitrogen containing Lewis base such as N,N-dimethyl-formamide or N,N-dimethyl-acetamide preferably in the presence of an alkali metal or alkaline earth metal carbonate, preferably calcium carbonate. The reaction may, for example, be effected at elevated temperatures, preferably at the reflux temperature of the solvent when used. Lower temperatures may be employed by using added lithium halide or calcium halide. This reaction is preferably effected using a 3$\alpha$-acyloxy-9$\alpha$-halo-11-oxo compound e.g. the 3$\alpha$-acetoxy compound, and where the corresponding 3$\alpha$-hydroxy compound is required, the 3$\alpha$-acyloxy-5$\alpha$-pregn-8-en-11-one produced may be reacted, for example, with a lower alkanol e.g. methanol or ethanol, or with water, preferably in the presence of an acid or base catalyst, for example perchloric acid. The reaction may be effected at a temperature of 0°–100°C.

The 9$\alpha$-halo-5$\alpha$-pregnan-11-ones used in the above reaction may be prepared by known methods and preferably by oxidation of the corresponding 3$\alpha$-acyloxy-9$\alpha$-halo-11$\beta$-hydroxy-5$\alpha$-pregnanes for example using chromic acid e.g. in a solvent such as acetone. These 3$\alpha$-acyloxy-9$\beta$-halo-5$\alpha$-pregnan-11$\beta$-ols may conveniently be prepared, for example by reaction of a compound of formula I wherein R$^4$ represents an epoxy group also linked to the 9$\beta$-position with a halogen hydracid, preferably hydrochloric acid.

In an alternative procedure, compounds of formula I wherein R$^3$ represent an acyl group which have a double bond between the 8- and 9-positions and an 11-oxo group may be prepared by oxidation of the corresponding 3$\alpha$-acyloxy-11$\beta$-hydroxy-5$\alpha$-pregn-8-ene for example using chromic acid as an oxidising agent e.g. in a solvent such as acetone. The 3$\alpha$-acyloxy compound required for this reaction may be prepared, for example, by dehydrohalogenation of the corresponding 3$\alpha$-acyloxy-9$\alpha$-halo-11$\beta$-hydroxy-5$\alpha$-pregnane referred to above.

Compounds of formula I wherein R$^2$ and R$^3$ are hydrogen may be prepared from the corresponding 3-oxo compound by stereospecific reduction e.g. as described by Browne and Kirk (*J. Chem. Soc.* C, 1969, 1653) using chloroiridic acid.

The latter reduction may also be carried out by use of a pre-formed iridium catalyst reduction system. For example, a reduction system may be prepared from an iridium acid or salt (e.g. chloriridic acid), a phosphorous acid ester (e.g. trimethyl phosphite), water and an organic reaction medium (e.g. an alcohol such as isopropanol); neutralised with an organic base (e.g. triethylamine) and reacted with the steroid.

Compounds of formula I wherein R$^1$ is an alkyl group may be prepared from corresponding 2$\alpha$,3$\alpha$-epoxy-5$\alpha$-pregnanes or androstanes by reaction with a metal alkyl, e.g. a lithium di-alkyl cuprate, to yield a 2$\beta$-alkyl-3$\alpha$-hydroxy 5$\alpha$-pregnane or androstane, followed by oxidation to a 2$\beta$-alkyl-5$\alpha$-pregn-3-one or a 2$\beta$-alkyl-5$\alpha$-androstan-3-one, equilibration to a 2$\alpha$-alkyl-5$\alpha$-pregn-3-one or 2$\alpha$-alkyl-5$\alpha$-androstan-3-one and stereospecific reduction to a 2$\alpha$-alkyl-3$\alpha$-hydroxy-5$\alpha$-pregnane or 2-6$\beta$ -alkyl-3$\alpha$-hydroxy-5$\alpha$-androstane respectively. In the case of 2$\alpha$-methyl compounds, these may be prepared, for example, from the corresponding 5$\alpha$-pregnan-3-one 20- ketals or 5$\alpha$-androstan-3-ones by reaction with an alkylformate, for example ethyl formate in the presence of an alkali metal hydride, for example sodium hydride to yield a 2-hydroxymethylene-5$\alpha$-pregnan-3-one 20-ketal or 5$\alpha$-androstan-3-one and reduction by catalytic hydrogenation and hydrogenolysis to yield a 2$\alpha$-methyl-5$\alpha$-pregnan-3-one or 2$\alpha$-methyl-5$\alpha$-androstan-3-one respectively. Thereafter the 3-oxo group is reduced stereospecifically, for example as described above by a method such as that disclosed by Browne and Kirk. Alternatively the 2-hydroxymethylene-3-one or 2$\beta$-alkyl-3-one in either the pregnane or androstane series may be reacted with chloroiridic acid to yield a 2$\alpha$-methyl-3$\alpha$-hydroxy-5$\alpha$-pregnane or androstane respectively.

Alternatively, the known 2$\alpha$-alkyl-3-ketones may be reduced, e.g. using a borohydride reducing agent, for example sodium borohydride, to give a 2$\alpha$-alkyl-3$\beta$-ol which may then be converted to the 3$\alpha$-ol by the method of Negata set out above.

Compounds of formula I wherein R$^1$ represents a halogen atom may be prepared by known methods. In general we have found it convenient to prepare such compounds by reacting the corresponding 2$\beta$-halo compound with an alkali metal halide, for example a lithium halide. When it is desired to introduce, for example, a bromine atom in the 2$\alpha$-position an alkali metal bromide is preferably used, advantageously lithium bromide. The reaction is preferably effected in an organic solvent such as a lower aliphatic ketone e.g. acetone or a di-lower alkyl lower acylamide e.g. dimethylformamide or dimethylacetamide, conveniently under reflux. The 2$\beta$-halo compounds required for this reaction may be prepared by reaction of a corresponding 2$\alpha$,3$\alpha$-epoxy-5$\alpha$-pregnane or androstane with a hydrogen halide, preferably in concentrated aqueous solution. A two-phase system in which the epoxide is dissolved in a water immiscible solvent, e.g. methylene chloride or chloroform may also be used.

The 2$\alpha$-halo compounds of the invention may also be prepared by the stereospecific reduction of the corresponding 2$\alpha$-halo-3-oxo compound, for example by use of the iridium catalyst technique described above.

Compounds according to the invention having a 3$\alpha$-oxygenated-5$\alpha$-androst-1-ene or pregn-1-ene structure may be prepared by known methods, preferably by dehydrohalogenation of the corresponding 3$\alpha$-oxygenated-2$\beta$-halo-5$\alpha$-androstane or pregnane compounds, for example the 2$\beta$-bromo compounds.

The dehydrohalogenation may be effected, for example using a nitrogen containing Lewis base such as a di-lower alkyl lower acylamide e.g. dimethylformamide or dimethylacetamide advantageously in the presence of an alkali metal or alkaline earth metal carbonate, for example calcium carbonate.

In general it has been found convenient to effect the dehydrohalogenation at an elevated temperature for example from 80° to 170°C. Lower temperatures may be employed when a lithium or calcium halide is present.

The above-described dehydrohalogenation may be effected, for example, using 3α-acyloxy or 3α-hydroxy-2β-halo-5α-pregnanes or androstanes. When it is desired to prepare a 3α-hydroxy-5α-pregn-1-ene or androst-1-ene from a corresponding 3α-acyloxy compound it may be convenient, for example first to prepare the 3α-acyloxy compound and subsequently to convert the 3α-acyloxy group thereof into a 3α-hydroxy group by known methods. In a preferred method, the conversion is effected by reaction with a lower alkanol, for example methanol or ethanol, or with water in the presence of an acid or of a base such as an alkali metal hydroxide, carbonate or bicarbonate for example potassium or sodium hydroxide, carbonate or bicarbonate. The lower alkanol may conveniently serve as an organic solvent for the reaction; the reaction is preferably effected at a temperature of 15°–40°C when an alkali metal hydroxide is used as the base and preferably at a temperature of 50°–100°C when an alkali metal carbonate or bicarbonate are used as the base.

Alternatively, the 3α-hydroxy group may be protected by a tetra hydropyranyl ether group during the preparation e.g. by reaction with dihydropyran with an acid catalyst, and removed subsequently e.g. by acid hydrolysis.

Compounds of formula I having an alkyl group in the 3β-position may be prepared by any convenient method. It has been found generally convenient, for example, to prepare such compounds from the corresponding 3-spiro-2'-oxirane by reaction with either a complex metal hydride, when it is desired to prepare compounds of formula I wherein $R^2$ represents a methyl group, or a metal alkyl e.g. lithium dimethyl cuprate, when it is desired to prepare compounds of formula I wherein $R^2$ represents an alkyl group other than a methyl group. The reaction with a metal alkyl is conveniently effected in an aprotic organic solvent, preferably an etheric solvent such as diethyl ether or tetrahydrofuran. In general it is preferred to effect the reaction at below ambient temperature, for example at a temperature of from −20° to +20°C.

The reaction of the 3-spiro-2'-oxirane compound with a complex metal hydride, preferably a complex aluminum hydride e.g. lithium aluminum hydride, is preferably effected in an aprotic organic solvent, for example an etheric solvent such as diethyl ether or tetrahydrofuran. In general, when an 11-oxo group is present in the compound reacted with the complex metal hydride it will be reduced to an 11β-hydroxy group. If it is desired to prepare compounds of formula I wherein $R^4$ and $R^5$ together represent an oxygen atom, the 11β-hydroxy compound produced in the above reaction may be oxidised by a known method, for example using chromic acid in an aqueous organic solvent, for example aqueous acetone. The oxidation is preferably effected under acidic conditions and advantageously at a temperature of 0°–50°C.

It may be desirable first to protect a 20-oxo group when present in a 3-spiro-2'-oxirane-20-oxo-pregnane compound when used in these reactions, for example by ketal formation e.g. with ethylene glycol.

The 3-spiro-2'-oxirane compounds used in the above reactions may be prepared in known manner. In general, it has been found convenient to prepare these compounds by reacting the corresponding 5α-pregnane-3,20-dione 20-ketal, preferably the 20-ethylenedioxy compound, with a trimethyl sulphoxonium halide, preferably the iodide, in the presence of an alkali metal hydride, preferably sodium hydride. The 3-spiro-2'-oxirane compounds may also be prepared, for example, by epoxidation of the corresponding 3-methylene compound by known methods.

Compounds according to the invention wherein $R^2$ represents an alkyl group and $R^3$ represents a hydrogen atom may also be prepared by reacting a corresponding 5α-pregna-3,20-dione 20-ketal with an alkyl magnesium halide preferably under conditions used for effecting Grignard reactions.

Compounds according to the invention wherein $R^6$ represents a halogen atom in the 16α-position may be prepared by known methods, for example from the corresponding 16-position unsubstituted 5α-pregn-16-ene by reaction with a halogen hydracid. The reaction with the halogen hydracid is advantageously effected in an anhydrous aprotic organic solvent such as an etheric solvent, for example 1,4-dioxan, diethyl ether or tetrahydrofuran. The reaction may conveniently be effected at about a temperature of 15°–40°C.

Compounds according to the invention containing a 17β-lower alkoxy carbonyl group may be prepared by known methods. We have found it convenient, for example, to prepare such compounds by reacting a salt of the corresponding 17β-carboxylic acid conveniently a tertiary amine salt or a quarternary ammonium salt (e.g. on trialkyl-ammonium salt or tetra-alkyl ammonium salt) with an alkyl halide corresponding to the alcohol portion of the desired ester, e.g. methyl iodide. This reaction is conveniently effected in a solvent medium [e.g. a lower alkyl ketone (such as acetone or methyl ethyl ketone) or dimethyl formamide] at temperatures of from 20° to 100°C.

We have found it generally convenient, particularly for the preparation of lower alkyl esters, to react the carboxylic acid with a diazoalkane, for example diazomethane or diazoethane. The reaction with the diazoalkane is conveniently effected in solution in an inert organic solvent, for example an ether such as diethyl ether or tetrahydrofuran, or a lower alkanol e.g. methanol, the diazo compound itself preferably being used in solution in an inert organic solvent, for example the solvent into which it is extracted during its preparation e.g. diethyl ether. The reaction is conveniently effected at temperatures between −25°C and +30°C.

The 17β-alkoxycarbonyl compounds according to the invention may also be prepared, for example, by reacting the corresponding 17β-carboxylic acid or a reactive derivative thereof with an alcohol in the presence of a catalyst. Acid catalysts have been found to be convenient e.g. sulphuric, hydrochloric, perchloric or p-toluene sulphonic acid. In one preferred method, the carboxylic acid is dissolved in an excess of the alcohol from which the ester is derived, for example, methanol, ethanol or isopropanol containing dry hydrogen chloride, advantageously at an elevated temperature, for example under reflux.

Suitable activated derivatives of the 17β-carboxyl compounds according to the invention include, for example, acid halides, preferably the acid chloride.

The reaction of the acid halide with an alcohol may be effected in known manner, preferably in the presence of an inert organic solvent, for example, a halogenated hydrocarbon e.g. methylene chloride or chloroform, an aromatic hydrocarbon, e.g. benzene or an ether e.g. diethyl ether or tetrahydrofuran.

In general, the reaction is preferably effected in the presence of an acid binding agent, for example, a tertiary organic base such as pyridine or triethylamine or an inorganic base such as an alkali metal carbonate or bicarbonate e.g. sodium carbonate or bicarbonate.

The reaction of the carboxylic acid halide with the alcohol may for example be effected at temperatures between −20°C to +110°C.

The acid halides used in the above reaction may be prepared by conventional methods, for example, from the corresponding 17β-carboxylic acid by reaction with a suitable halogenating agent e.g. a thionyl, phosphoryl or oxalyl halide. When it is desired to use the acid chloride for the preparation of the esters according to the invention, thionyl chloride, phosphoryl chloride or oxalyl chloride are preferably used. The 3α-hydroxy group is preferably protected during this reaction.

The carboxylic acids required for the above-described reaction may be prepared by known methods, for example by oxidation of the 17β-acetyl group of a corresponding pregnane. This oxidation may for example be effected in solution using a hypohalite e.g. an alkali metal or alkaline earth metal hypohalite as oxidising agent. Suitable hypohalites include, for example, sodium and potassium hypochlorites, hypobromites and hypoiodites.

The oxidation process is conveniently carried out in aqueous or non-aqueous media. Thus the reaction may for example be effected in an aqueous water-miscible organic solvent for example a water-miscible ether e.g. dioxan, tetrahydrofuran, diglyme or 1,2-dimethoxyethane or a water-miscible alcohol e.g. t-butanol. The preferred solvent is dioxan.

The oxidation may be effected at a temperature of from −20° to 100°C, a temperature of from 5° to 10°C being preferred.

In order that the invention may be well understood the following examples are given by way of illustration only. In the Examples rotations are for ca. 1% w/v solutions in chloroform at 20°C. Throughout the Examples the term petroleum ether refers to petroleum ether b.p. 40° to 60°C. All temperatures are in degrees Celsius. Preparative thin layer chromatography (preparative t.l.c) was carried out on silica gel.

EXAMPLE 1

3α-Trichloroacetoxy-5α-pregnane-11,20-dione

A solution of trichloroacetyl chloride (0.5 ml.) in dry tetrahydrofuran (8 ml.) was added dropwise to a cooled (−80°) and stirred solution of 3α-hydroxy-5α-pregnane-11,20-dione (0.75 g.) and pyridine (0.35 ml.) in dry tetrahydrofuran (15 ml.). After 30 min. the mixture was concentrated in vacuo and the residue was partitioned between ethyl acetate and water. The organic layer was washed with 2N-hydrochloric acid, aqueous sodium hydrogen carbonate, then water. The solution was dried and concentrated to leave a residue which was crystallised from benzene then benzene-petrol to afford the title compound (0.21 g.), m.p. 126°–127°, $[\alpha]_D + 86°$.

EXAMPLE 2

3α-Trifluoroacetoxy-5α-pregnane-11,20-dione

A solution of trifluoroacetic anhydride (0.34 ml.) and pyridine (0.24 ml.) in methylene dichloride (10 ml.) was added to a cooled (−80°) and stirred solution of 3α-hydroxy-5α-pregnane-11,20-dione (0.50 g.) in methylene dichloride (20 ml.) and the mixture was allowed to warm up to room temperature. After 1½ hours more trifluoroacetic anhydride (0.34 ml.) was added and the reaction was complete after ½ hour more. The solution was washed successively with water, sodium bicarbonate solution and water. The dried and concentrated solution afforded a crystalline residue that was triturated with petroleum to give the title compound as needles (0.44 g.) m.p. 107°–108°, $[\alpha]_D + 96°$.

EXAMPLE 3

3α,11β-Dihydroxy-11α-methyl-5α-pregnan-20-one 20,20-Ethylenedioxy-3α-hydroxy-5α-pregnan-11-one (750 mg.) in dry tetrahydrofuran (20 ml.) was added under nitrogen to a stirred solution of 2M methyl lithium in ether (10 ml.) containing dry tetrahydrofuran (10 ml.). After 3 hr. at room temperature 10% ethanol in tetrahydrofuran (20 ml.) was added, followed by 6N hydrochloric acid (5 ml.). After 1 hr., ether was added and the mixture was washed with water dried ($Na_2SO_4$) and evaporated to a gum which crystallised from chloroform/ether to give the title compound (203 mg.) as colourless needles, m.p. 170°–174°; $[\alpha]_D + 94°$.

EXAMPLE 4 a.

3β-Hydroxy-16-methyl-5α-pregn-16-ene-11,20-dione

3β-Acetoxy-16-methyl-5α-pregn-16-ene-11,20-dione (4.25 g.) in methanol (70 ml.) was treated with 20% aqueous potassium hydrogen carbonate solution (20 ml.) and heated under reflux for 5 hr. Water (15 ml.) was added, and solvent removed until the bulk of the product had precipitated. Addition of excess water and filtration gave the title compound (3.57 g.) m.p. 222°–223.5°, which on crystallisation from methanol gave the alcohol as spars, m.p. 224°–224.5°, $[\alpha]_D + 35.2°$.

b.

3α-Acetoxy-16-methyl-5α-pregn-16-ene-11,20-dione

Toluene-p-sulphonyl chloride (8 g.) was added to a solution of the above alcohol (9 g.) in dry pyridine (60 ml.) and the mixture was kept at room temperature for 21 hours. Water (6 ml.) was added and after the solution had been stirred for 2½ hours it was poured into ice-cold dilute hydrochloric acid (700 ml.). The solid was filtered off, dried and recrystallised from ethyl acetate/petrol to give 3β-(toluene-p-sulphonyloxy)-16-methyl-3α-pregn-16-ene-11,20-dione as fine needles (8.8 g.) m.p. 166°, $[\alpha]_D + 14.1°$.

A solution of this (8.5 g.) and tetraethyl-ammonium acetate (6.47 g.) in butan-2-one (170 ml.) was heated under reflux for 17 hours. More tetraethyl-ammonium acetate (1.0 g.) was added and the heating was continued for a further 6 hours. Solvent was removed in vacuo and the residue was dissolved in chloroform (70 ml.). This solution was washed with water, dried and concentrated in vacuo. The residue was extracted with refluxing ether and the remaining solid was crystallised from ether to give the title compound as small plates (1.3 g.), m.p. 200°–208°, $[\alpha]_D + 44.5°$ c. 3α-Hydroxy-16β-methyl-5α-pregnane-11,20-dione A solution of the foregoing 3α-acetate (2.09 g.) in dioxan (130 ml.) was flushed with nitrogen. Solid potassium hydroxide (1.0 g.) was added and then nitrogen-flushed water (30 ml.) was added to give a clear solution which was kept at 48° for 4 hours and room temperature for 18½ hours. Glacial acetic acid was added to bring the pH to 6.0 and then solvents were removed in vacuo at 48° until crystallisation commenced. Water (400 ml.) was then slowly added and the solid filtered off. A solution of the solid in chloroform was filtered through neutral alumina (grade III). Removal of solvent in vacuo left a solid that was crystallised from acetone-petrol to give 3α-hydroxy-16-methyl-5α-pregn-16-ene-11,20-dione as small rods (1.21 g.), m.p. 230°–231°, $[\alpha]_D + 41°$.

A solution of this (0.8 g.) in tetrahydrofuran (50 ml.) containing 5% palladised charcoal (0.4 g.) was shaken in an atmosphere of hydrogen for 48 minutes. The catalyst was filtered off on a Kieselguhr pad and the solvent was evaporated off in vacuo to leave a solid that was recrystallised from acetone-petroleum to give the title compound as small rods (0.64 g.) m.p. 186°–189°, $[\alpha]_D + 64.5°$.

EXAMPLE 5 a. 3β-Hydroxy-5α-pregna-9(11),16-dien-20-one

A solution of potassium hydroxide (25 g.) in water (50 ml.) was added to a solution of 3β-acetoxy-5α-pregna-9,16-dien-20-one (25 g.) in t-butanol (1.25 l) and the mixture was refluxed for 16 hours. About ¾ of the solvent was evaporated off and water (ca. 4 liters) was added. The precipitate was filtered off and dried to give the title compound as an off-white solid (21.4 g), m.p. 188°–190°, $[\alpha]_D + 121°$.

b. 3α-Hydroxy-5α-pregna-9,16-dien-20-one

A solution of toluene-p-sulphonyl chloride (23.2 g.) and the above 3β-alcohol (21 g.) in pyridine (118 ml.) was kept at room temperature for 20 hr. Sufficient water was added to dissolve the pyridine hydrochloride and the solution was kept for 2 hr. Dilute hydrochloric acid was added and the gum was extracted into chloroform. The chloroform extract was washed with hydrochloric acid, sodium bicarbonate solution and water, dried and concentrated to give a syrup. This was dissolved in benzene and filtered through a pad of neutral alumina. Crystallisation from ethyl acetate-petroleum ether and recrystallisation from benzene-petroleum ether gave 3β-(toluene-p-sulphonyloxy)-5α-pregna-9,16-dien-20-one as a pale yellow solid m.p. 80°–90° (decomp.) $[\alpha]_D + 32°$.

A solution of the tosylate (10 g.) in dimethyl-formamide (375 ml.) and water (5 ml.) was heated at 115° for 16 hours and then poured into iced-water (2 l). This was extracted with methylene chloride and the extract was washed with water, dried, and concentrated. Vestigial dimethylformamide was removed under high vacuum to leave the crude 3α-formyloxy-5α-pregna-9,16-dien-20-one as a solid residue (6 g.). A solution of the crude formate (5.7 g.) in t-butanol (500 ml.) which was stirred with a solution of potassium carbonate (2.3 g.) in water (23 ml.) for 2½ hours. More potassium carbonate (2.3 g.) in water (23 ml.) was added, the mixture was kept at 50° for 2 hours whereupon a solution of potassium hydroxide (5.7 g.) in water (10 ml.) was added. After 30 minutes acetic acid was added to bring the pH to 5. Solvent was then evaporated off until crystallisation began, whereupon water was added to complete the precipitation. The solid was filtered off, dried and extracted with petrol. The residue (4.44 g.) was recrystallised from ether to give the title compound as prisms (1.69 g.) m.p. 213°–221°, $[\alpha]_D + 130°$.

c. 3α-Hydroxy-5α-pregn-9(11)-en-20-one

A solution of the above diene (4.0 g.) in ethyl acetate (500 ml.) containing triethylamine (22.4 ml) was shaken with 5% palladised charcoal (0.4 g.) in an atmosphere of hydrogen for 40 minutes. The catalyst was filtered off on a Kieselguhr pad and the filtrate was concentrated to dryness. The residue was triturated with methanol (50 ml.) and the resulting slurry treated with a 10% acetic acid solution (22 ml.). The solid (2.78 g.) was filtered off, washed with water and dried. Chromatography on neutral alumina (Grade III) and crystallisation from ether-petrol gave the title compound as needles (1.32 g.) m.p. 160°–161°, $[\alpha]_D + 103°$.

EXAMPLE 6

9β,11β-Epoxy-3α-hydroxy-5α-pregnan-20-one

3α-Hydroxy-5α-pregn-9(11)-en-20-one (500 mg.) was dissolved in dioxan (50 ml.) and water (12.5 ml.) under nitrogen; N-bromosuccinimide (325 mg.) was added followed by perchloric acid (60% w/v; 0.175 ml.) in water (5 ml.) and the reaction was allowed to stand at room temperature for 5 min. The pH was adjusted to 11.7 with 2N sodium hydroxide and the reaction mixture was allowed to stand at room temperature for a further 15 mins. The pH was adjusted to 6 with glacial acetic acid and the mixture was poured into water. The steroid was extracted with chloroform and triturated with ether to give a white solid; crystallisation from ether followed by crystallisation from methyl acetate-petrol gave the title compound (134 mg.), m.p. 160°–162°, $[\alpha]_D + 101°$.

EXAMPLE 7

3α-Acetoxy- 5α-pregn-9(11)-en-20-one

3α-Hydroxy-5α-pregn-9(11)-en-20-one (3.7 g.) was dissolved in pyridine (37 ml.) and acetic anhydride (18.5 ml.) added; the reaction was allowed to stand at room temperature for 66 hr. It was then poured into water (4 l.) and stored at 2° for 2 hr., the white solid was filtered off and dried to give the title compound (3.8 g.) m.p. 163°–165°.

EXAMPLE 8

3α-Acetoxy-9β,11β-epoxy-5α-pregnan-20-one

3α-Acetoxy-5α-pregn-9(11)-en-20-one (3 g.) was dissolved in dioxan (300 ml.) and water (75 ml.); N-bromosuccinimide (2.1 g.) was added followed by perchloric acid (60% w/v; 1.05 ml.) in water (30 ml.) and the reaction allowed to stand at room temperature under nitrogen for 5 min. The pH was adjusted to 11.7 with 2N sodium hydroxide and the reaction mixture was allowed to stand at room temperature under nitrogen for a further 15 min; the pH was adjusted to 6 with glacial acetic acid and the mixture was poured into water. The steroid was extracted with ether to give a crystalline solid (3.2 g.); crystallisation from ether-petrol followed by recrystallisation from aqueous methanol gave the title compound m.p. 133°–136°, $[\alpha]_D$ + 105°.

EXAMPLE 9

3α-Acetoxy-5α-pregn-8-ene-11,20-dione a. 3α-Acetoxy-9α-chloro-11β-hydroxy-5α-pregnan-20-one 3α-Acetoxy-9β,11β-epoxy-5α-pregnan-20-one (500 mg.) was dissolved in ether and the ether evaporated to leave a gummy residue. Hydrochloric acid (11.6N; 5ml.) was added and the reaction stirred for 4 min., it was then poured into aqueous sodium bicarbonate solution and the solid filtered off, washed with water and dried. Crystallisation from methyl acetate-petrol gave the title compound (250 mg.), m.p. 175°–179°. Recrystallisation from aqueous acetone gave a sample m.p. 177°–179°, $[\alpha]_D$ + 97°.

b. 3α-Acetoxy-5α-pregn-8-ene-11,20-dione

The above chlorohydrin (850 mg.) was dissolved in acetone (45 ml.) and chromic acid (ca. 8N; 2.1 ml.) was added. The reaction was stirred under nitrogen at <10° for 25 min., it was then poured into aqueous sodium bicarbonate solution and the precipitate filtered, washed with water and dried to give 3α-acetoxy-9α-chloro-5α-pregnane-11,20-dione (760 mg.). Crystallisation twice from aqueous acetone gave a sample m.p. 151°–154°, $[\alpha]_D$ + 174°.

This compound (750 mg.) was dissolved in dimethylacetamide (75 ml.) and finely divided calcium carbonate (1.5 g.) added. The reaction mixture was refluxed for 30 min., filtered and the solvent evaporated off under reduced pressure to give the title compound (650 mg.). Crystallisation twice from aqueous methanol gave a sample, m.p. 169°–172°, $[\alpha]_D$ + 218°.

EXAMPLE 10

3α-Hydroxy-5α-pregn-8-ene-11,20-dione

3α-Acetoxy-5α-pregn-8-ene-11,20-dione (400 mg.) was dissolved in methanol (40 ml.) and perchloric acid (60% w/v; 2 ml.) was added and the solution was allowed to stand at room temperature for 19 hours. The reaction mixture was poured into water and the steroid extracted with chloroform. The solvent was removed from the extract and the residue twice crystallised from methyl acetate-petrol to give the title compound (135 mg.) m.p. 170°–172°, $[\alpha]_D$ + 250°.

EXAMPLE 11

2α-Bromo-3α-hydroxy-5α-pregnane-11,20-dione

2α, 3α-Epoxy-5α-pregnane-11,20-dione (502 mg) was dissolved in chloroform (30 ml.) and the solution was treated with hydrobromic acid (48 %, 10 ml.). The mixture was stirred vigorously at room temperature for 30 minutes, and then poured into chloroform. The organic solution was washed with dilute sodium bicarbonate solution, then with water, and was then dried over sodium sulphate and evaporated to give a crystalline residue which was recrystallised from acetone-ether to give 2β-bromo-3α-hydroxy-5α-pregnane-11,20-dione (483 mg.) as colourless crystals, m.p. 206°–210° $[\alpha]_D$ + 106°.

A solution of this (330 mg.) in acetone (3 ml.) was treated with lithium bromide (454 mg.), and the mixture was refluxed for 18 hr. The reaction mixture was poured into water, and the product extracted with methylene chloride. The extract was washed with water, dried ($Na_2SO_4$), and evaporated in vacuo. The residue (277 mg.) was subjected to preparative t.l.c. to give two fractions. The less polar fraction was the title compound (37 mg.) with a nuclear magnetic resonance spectrum resembling that of the second product of Example 12.

EXAMPLE 12

3α-Hydroxy-5α-pregn-1-ene-11,20-dione and 2α-bromo-3α-hydroxy-5α-pregnane-11,20-dione A solution of 2β-bromo-3α-hydroxy-5α-pregnane-11,20-dione (2.5 g.) in dry dimethyl acetamide (70 ml.) was treated with lithium bromide (9.3 g.) and finely divided calcium carbonate (7.1 g.), and the mixture was stirred on a steam bath for 4½ hr. The reaction mixture was cooled to room temperature, filtered, treated with 2N HCl to pH 4, and the product was extracted with methylene chloride. The extract was washed with water, dried ($Na_2SO_4$), and evaporated in vacuo. The residue (2.3 g.) was subjected to preparative t.l.c. The most polar fraction was 3α-hydroxy-5α-pregn-1-ene-11,20-dione (305 mg., 15%), with a nuclear magnetic resonance spectrum resembling that of the product of Example 17. The least polar fraction, after crystallisation from methyl acetate/petrol, gave 2α-bromo-3α-hydroxy-5α-pregnane-11,20-dione (53 mg.), m.p. 168°–170°, $[\alpha]_D$ + 134.5°.

EXAMPLE 13 a. 3α-Acetoxy-2β-bromo-5α-pregnane-11,20-dione

2β-Bromo-3α-hydroxy-5α-pregnane-11,20-dione (750 mg.) in pyridine (2 ml.) was treated with acetic anhydride (1 ml.) and the mixture was allowed to stand at room temperature overnight. It was then poured into water to give a white solid (720 mg.) which was recrystallised from methanol to give 3α-acetoxy-2β-bromo-5α-pregnane-11,20-dione (471 mg.) as white crystals, m.p. 154°–156°, $[\alpha]_D$ + 128.5°.

b. 3α-Acetoxy-5α-pregn-1-ene-11,20-dione

A solution of the above acetate (9.1 g.) in dry dimethyl acetamide (255 ml.) was treated with lithium bromide (34.0 g.) and finely divided calcium carbonate (26.2 g.), and the mixture was stirred on a steam bath for 3 hr. The reaction mixture was cooled to room temperature, filtered, treated with 2N HCl to pH 4, and the product extracted with methylene chloride. The extract was washed with water, dried ($Na_2SO_4$), and evaporated under reduced pressure. A portion (460 mg.) of the residue (8.5 g.) was purified by preparative t.l.c. and crystallisation from iso-propyl ether to give the title compound (188 mg.), m.p. 145°–147°, $[\alpha]_D$ + 33.8°. The residue also contained 3α-acetoxy-2α-bromo-5α-pregnane-11,20-dione, as evidenced by the formation of the corresponding 3α-ol in Example 14 (b).

EXAMPLE 14

3α-Hydroxy-5α-pregn-1-ene-11,20-dione a. A solution of 3α-acetoxy-5α-pregn-1-ene-11,20-dione (7.9 g.) in dry methanol (225 mg.) was treated with potassium bicarbonate (8.5 g.), and the mixture was refluxed under nitrogen for 1½ hr. The reaction mixture was concentrated in vacuo, then poured into water, and the product was extracted with methylene chloride. The extract was washed with water, dried ($Na_2SO_4$), and evaporated in vacuo. The residue (6.0 g.) was purified by preparative t.l.c. and crystallisation from methyl acetate/petroleum ether to give the title compound (1.64 g.), m.p. 119°–121°, $[\alpha]_D$ + 56.8°.

b. A solution of crude 3α-acetoxy-5α-pregn-1-ene-11,20-dione (3.6 g.) in dry methanol (96 ml.) was treated with a solution of potassium hydroxide (650 mg.) in methanol (72 ml.), and the mixture stirred under nitrogen at room temperature for 2 hr. The reaction mixture was poured into water, and the product extracted with methylene chloride. The extract was washed with water, dried ($MgSO_4$), and evaporated in vacuo. The residue (3.1 g.) was subjected to preparative t.l.c. The more polar product afforded the title compound (1.66 g.), with an $R_F$ identical on t.l.c. to that of the product of (a).

The less polar product was 2α-bromo-3α-hydroxy-5α-pregnane-11,20-dione (363 mg.), m.p. 166°–169°, $[\alpha]_D$ + 138°.

EXAMPLE 15

3α-Acetoxy-5α-pregn-1-en-20-one a. 2β-Bromo-3α-hydroxy-5α-pregnan-20-one

2α, 3α-Epoxy-5α-pregnan-20-one (356 mg.) was dissolved in chloroform (20 ml.) and hydrobromic acid (48%, 7 ml.) was added. The mixture was stirred at room temperature for 30 minutes and then poured into chloroform (100 ml.). The organic solution was washed with dilute sodium bicarbonate solution and with water, then dried over sodium sulphate and evaporated to give a crystalline residue which was recrystallised from ethyl acetate containing some ether to give title compound (144 mg.) as colourless needles m.p. 171°–175°, $[\alpha]_D$ + 117°.

b. 3α-Acetoxy-5α-pregn-1-en-20-one

A solution of 3α-hydroxy-2β-bromo-5α-pregnan-20-one (8.5 g.) in pyridine (25 ml.) was treated with acetic anhydride (12.5 ml.), and the mixture was allowed to stand at room temperature overnight. The reaction mixture was poured into water and the product was extracted with methylene chloride. The extract was washed with water, dried ($Na_2SO_4$) and evaporated. A portion (582 mg.) of the residue (8.5 g.) was purified by preparative t.l.c. and crystallisation from iso-propyl ether to give 3α-acetoxy-2β-bromo-5α-pregnan-20-one (70 mg.), 142°–146°, $[\alpha]_D$ + 120.9°.

A solution of this (7.9 g.) in dry dimethylacetamide (218 ml.) was treated with lithium bromide (30.0 g.) and calcium carbonate (22.4 g.), and the mixture stirred on a steam bath for 4 hours. The reaction mixture was cooled to room temperature, filtered, treated with 2N HCl to pH 4, and the product extracted with methylene chloride. The extract was washed with water, dried ($Na_2SO_4$), and evaporated in vacuo. The residue (6.9 g.) was purified by preparative t.l.c. to give the title compound (4.4 g). The residue also contained some 3α-acetoxy-2α-bromo-5α-pregnan-20-one, as evidenced by hydrolysis to the corresponding 3α-ol in Example 18.

EXAMPLE 16

3α-Hydroxy-5α-pregn-1-en-20-one and 2α-bromo-3α-hydroxy-5α-pregnan-20-one

A solution of crude 3α-acetoxy-5α-pregn-1-en-20-one (4.0 g.) containing some 3α-acetoxy-2α-bromo-5α-pregnan-20-one, in dry methanol (120 ml.) was treated with potassium bicarbonate (4.5 g.), and the mixture was refluxed under nitrogen for 2 hours. The reaction mixture was concentrated in vacuo, then poured into water, and the product was extracted with methylene chloride. The extract was washed with water, dried ($Na_2SO_4$), and evaporated in vacuo. The residue (3.3 g.) was subjected to preparative layer chromatography. The more polar fraction, after crystallisation from methyl acetate, gave 3α-hydroxy-5α-pregn-1-en-20-one (780 mg), m.p. 150°–154°, $[\alpha]_D$ + 28.9°. The less polar fraction after crystallisation from methyl acetate, gave 2α-bromo-3α-hydroxy-5α-pregnan-20-one (320 mg), m.p. 201°–204°, $[\alpha]_D$ + 110.5°.

EXAMPLE 17

3α-Hydroxy-3β-methyl-5α-pregnane-11,20-dione

Methyl iodide (18.8 g.) was added slowly to a cooled, stirred mixture of magnesium (0.32 g.), ether (10 ml.) and a crystal of iodine. The resulting mixture was refluxed for 1 hr. under nitrogen. A solution of 5α-pregnane-3,11,20-trione 20-ketal (4.0 g.) in dry tetrahydrofuran (40 ml.) was then added dropwise. The resulting suspension was refluxed for 2 hr., treated with saturated aqueous ammonium chloride and partitioned between water and ethyl acetate. The organic layer was washed with water, dried ($Na_2SO_4$) and evaporated. The residue was subjected to preparative t.l.c. and the more polar component was fractionally crystallised from ethyl acetate/petroleum ether (60°–80°).

The more soluble fraction was identified as 20,20-ethylenedioxy-3α-hydroxy-3β-methyl-5α-pregnan-11-one (196mg), m.p. 138°, $[\alpha]_D$ + 56°.

A solution of this in a mixture of methanol (7.7 ml.) and acetone (2.6 ml.) was treated with 2N-hydrochloric acid (2.6 ml.) at room temperature for 6 hr. The mixture was partitioned between water and ether. The organic layer was washed with water, dried ($Na_2SO_4$) and evaporated. Recrystallisation of the residue from ether/petroleum ether (b.p. 60°–80°) afforded title compound (90 mg), as white needles, m.p. 175°, $[\alpha]_D$ + 116°.

EXAMPLE 18

3α-Hydroxy-3β-methyl-5α-pregnane-11,20-dione a.

(3R)-20-20-Ethylenedioxy-11-oxo-5α-pregnane-3-spiro-2'-oxirane

A mixture of sodium hydride (17 mg.), trimethyl-sulphoxonium iodide (300 mg.) and dimethyl sulphoxide (2 ml.) was stirred under nitrogen at room temperature for 1 hr. 5α-Pregnane-3,11,20-trione 20-ketal (100 mg.), was then added and the resulting mixture was stirred for a further 2 hr. and poured into water. The precipitated solid was collected by filtration, washed with water and dried over $P_2O_5$ in vacuo. Recrystallisation from acetone/petrol gave the title compound (50 mg.), as white needles, m.p. 176°–177°; $[\alpha]_D + 49°$.

b. 20,20-Ethylenedioxy-3β-methyl-5α-pregnane-3α,11β-diol

A solution of the above oxirane (1.0 g.) in tetrahydrofuran (5 ml.) was added to a stirred suspension of lithium aluminium hydride (0.5 g.) in ether (15 ml.). The resulting mixture was refluxed for 2 hr. treated with saturated aqueous ammonium chloride and partitioned between water and ether. The organic layer was washed with water, dried ($Na_2SO_4$) and evaporated. Recrystallisation of the residue from acetone gave the title compound (0.9 g., as white needles, m.p. 162°, $[\alpha]_D + 35°$.

c. 3α-Hydroxy-3β-methyl-5α-pregnane-11,20-dione

A solution of 20,20-ethylenedioxy-3β-methyl-5α-pregnane-3α,11β-diol (1.5 g.) in acetone (60 ml.) was treated with a solution of potassium dichromate (1.5 g.) in 2N-sulphuric acid (15 ml.) at room temperature for 2 hr. The mixture was then poured into water and the precipitated solid was collected by filtration, washed with water and dried over phosphorus pentoxide in vacuo. Recrystallisation from acetone-petroleum ether gave the title compound (0.75 g) as white needles, m.p. 175°; $[\alpha]_D + 116°$.

EXAMPLE 19

3β-Ethyl-3α-hydroxy-5α-pregnane-11,20-dione

A 2M solution of methyl lithium in ether (15.5 ml.) was added to a stirred slurry of cuprous iodide (3.0 g.) in ether (50 ml.) under nitrogen at −20°. A solution of (3R)-20,20-ethylenedioxy-11-oxo-5α-pregnane-3-spiro-2'-oxirane (1.0 g.) in ether (150 ml.) was then added to the mixture at −20°. The reaction was left at 0° for 18 hr., poured into saturated aqueous ammonium chloride and extracted with ethyl acetate. The extracts were washed with water, dried ($Na_2SO_4$) and evaporated. Preparative t.l.c. and recrystallisation from acetone afforded 3β-ethyl-20,20-ethylenedioxy-3α-hydroxy-5α-pregnan-11-one (1.7 g.), m.p. 144°, $[\alpha]_D + 72.3°$.

A solution of this (0.5 g.) in acetone (85 ml.) was treated with 2N-hydrochloric acid (17 ml.) at room temperature for 30 min. The solution was then poured into water and extracted with ethyl acetate. The extracts were washed with water, dried ($Na_2SO_4$) and evaporated. Recrystallisation of the residue from acetone gave the title compound (0.3 g.), m.p. 129° $[\alpha]_D + 118°$.

EXAMPLE 20

3α-Hydroxy-3β-pentyl-5α-pregnane-11,20-dione 20,20-Ethylenedioxy-3α-hydroxy-3β-pentyl-5α-pregnan-11-one (m.p. 106°, $[\alpha]_D + 62°$) was prepared in similar manner to the corresponding 3β ethyl compound of Example 21 using a 22% solution of butyl lithium in hexane in place of 2M methyl lithium in ether. Acid hydrolysis as described in Example 21 followed by recrystallisation from ether/petrol gave the title compound (0.14 g.), m.p. 102°; $[\alpha]_D + 109°$.

EXAMPLE 21

3α-Hydroxy-3β-methyl-5α-pregnan-20-one

This was prepared from 5α-pregnane-3,20-dione-20 ketal (3 g.) via 3(R)-20,20-ethylenedioxy-5α-pregnane-3-spiro-2'-oxirane and then 20,20-ethylenedioxy-3β-methyl-5α-pregnan-3α-ol (m.p. 139°) in a manner similar to that described in Example 20 for the preparation of 3α-hydroxy-3β-methyl-5α-pregnane-11,20-dione. The title compound (0.6 g.) was obtained as white needles m.p. 189°, $[\alpha]_D + 103°$.

EXAMPLE 22

16α-Chloro-3α-hydroxy-5α-pregnane-11,20-dione a. 3β-Hydroxy-5α-pregn-16-ene-11,20-dione A solution of 3β-acetoxy-5α-pregn-16-ene-11,20-dione (25.7 g.) in dioxan (500 ml.) was treated with potassium hydroxide (10 g.) and water (250 ml.) and the mixture allowed to stand at room temperature for 1 hour. After a further 1 hour at 40° the mixture was diluted with water and the product filtered off. The crude material was dissolved in chloroform and filtered through a column of grade III neutral alumina. Crystallisation from acetone-petrol gave pure 3β-hydroxy-5α-pregn-16-ene-11,20-dione (17.65 g.) as small plates m.p. 217.5°, $[\alpha]_D + 82.9°$. (c 1.1)

b. 16α-Chloro-3α-hydroxy-5α-pregnane-11,20-dione

A solution of 3β-hydroxy-5α-pregn-16-ene-11,20-dione (39.6 g) in dry pyridine (165 ml.) was treated with toluene-p-sulphonyl chloride (43.9 g.) to give 3β-toluene-p-sulphonyloxy-5α-pregn-16-ene-11,20-dione (56.7 g.) m.p. 147°–151°. A portion (10.7 g.) of this material was crystallised from ethyl acetate-petrol to give the pure toluenesulphonate (9.2 g.) as plates m.p. 154°–155°, $[\alpha]_D + 42.8°$ (c 1.2).

A solution of this (19.1 g.) in N,N-dimethyl-formamide (160 ml.) and water (16.0 ml.) was treated with potassium acetate (29.2 g.) and the mixture heated at 115° for 2½ hours. The solvents were removed in vacuo and the residue partitioned between chloroform and water. The chloroform extract was washed with water, dried and evaporated. The residue was taken up in methanol (500 ml.) and the solution flushed with nitrogen. Potassium hydroxide (17 g.) in water (70 ml.) was added and the solution refluxed for 1 hour. Glacial acetic acid was added to bring the pH to about 6 and most of the methanol evaporated in vacuo. Dilution with water gave a gummy precipitate which was extracted into chloroform to give the crude product. This material was extracted with ether and the residue boiled with benzene. The insoluble material was crystallised from chloroform-petrol to give 3α-hydroxy-5-pregn-16-ene-11,20-dione (3.28 g.) as large prisms m.p. 243°–244°, $[\alpha]_D + 86.5°$ (c 0.8).

c. Dry hydrogen chloride was passed through a solution of this (500 mg.) in dry 1,4-dioxan (40 ml.) for 1 hour. The solution was left to stand at room temperature for a further hour, and then poured slowly into cold saturated sodium bicarbonate solution (200 ml.), and the white precipitate was extracted into ether. The extract was washed with water, dried over sodium sulphate and evaporated to give an oil which was recrystallised from ethyl acetate and petrol (b.p. 60°–80°) to give a white crystalline product (430 mg.). This was purified by preparative t.l.c. in ethyl acetate and petrol (b.p. 60°–80°) and recrystallisation from ethyl acetate and petrol (b.p. 60°–80°) to give the title compound (200 mg.) as fine white needles, m.p. 226°–227°, $[\alpha]_D + 119°$.

EXAMPLE 23

3α-Hydroxy-2α-methyl-5α-pregnane-11,20-dione a.

20,20-Ethylenedioxy-2-hydroxmethylene-5α-pregnane-3,11-dione

Sodium hydride (0.13 g.) was added, with stirring, to a cooled solution of 20,20-ethylenedioxy-5α-pregnane-3,11-dione (0.3 g.) and ethyl formate (0.3 ml.) in dry benzene (6 ml.) under nitrogen. The reaction mixture was kept at room temperature for 24 hr. and then evaporated to dryness in vacuo. Aqueous hydrochloric acid (2N) was added to the residue and after stirring for 30 minutes the solid (0.33 g.) was collected by filtration. Treatment with charcoal and crystallisation from methyl acetate/petrol (b.p. 60°–80°) gave title compound (0.126 g.), m.p. 149°–151°, $[\alpha]_D + 121°$ (c 0.5).

b.

20,20-Ethylenedioxy-2α-methyl-5α-pregnane-3,11-dione

A mixture of 20,20-ethylenedioxy-2-hydroxymethylene-5α-pregnane-3,11-dione (6 g.), palladium-on-charcoal (10%, 2.5 g.) and ethyl acetate (250 ml.) was shaken under hydrogen for 5½ hr. The mixture was then filtered through Kieselguhr and the filtrate was evaporated to dryness (6.1 g.) in vacuo. A portion of the residue (3 g.) was subjected to preparative t.l.c. The less polar fraction (0.59 g.) was crystallised from methanol to give title compound (0.35 g.), m.p. 168°–169°.

The more polar fraction (0.62 g.) was crystallised from methanol to give 20,20-ethylenedioxy-2β-methyl-5α-pregnane-3,11-dione (0.44 g) m.p. 140°–142°, $[\alpha]_D + 142°$.

c. 2α-Methyl-5α-pregnane-3,11,20-trione

A solution of the above ketal (0.39 g.) and toluene-p-sulphonic acid (30 mg.) in acetone (30 ml.) was kept at room temperature for 1½ hr.

The solution was then evaporated to low bulk and an aqueous solution of sodium hydrogen carbonate added. The solid was collected by filtration. Crystallisation from methyl acetate/petrol (b.p. 60°–80°) gave the title compound (0.21 g.) m.p. 176°, $[\alpha]_D + 136°$.

d. 3α-Hydroxy-2α-methyl-5α-pregnane-11,20-dione

A solution of chloroiridic acid (75 mg.) and trimethyl phosphite (3 ml.) in aqueous isopropanol (90%, 40 ml.) was heated under reflux for 17 hr.

A portion of this reaction mixture (10 ml.) and 2α-methyl-5α-pregnane-3,11-20-trione (0.27 g.) were heated together under reflux for 70 hrs. The reaction mixture was then partitioned between water and methylene chloride. The organic layer was dried (MgSO₄) and evaporated and the residue was purified t.l.c. and crystallisation from methyl acetate/petrol (b.p. 60°–80°) to give the title compound (0.083 g., m.p. 177°–178°, $[\alpha]_D + 132°$.

EXAMPLE 24

20,20-Ethylenedioxy-2α-methyl-5α-pregnane-3,11-dione and
20,20-ethylenedioxy-3α-hydroxy-2α-methyl-5α-pregnan-11-one A solution of chloroiridic acid (30 mg.) and trimethyl phosphite (4.5 ml.) in aqueous 90% isopropanol (60 ml.) was heated under reflux for 17 hr. The solution was then neutralised with triethylamine and 20,20-ethylenedioxy 2-hydroxymethylene-5α-pregnane-3,11-dione (2 g.) was added. The mixture was heated under reflux for 40 hr. then cooled and partitioned between water and methylene chloride. The organic layer was dried (MgSO₄) and evaporated in vacuo. The residue (1.94 g.) was subjected to preparative t.l.c. giving two fractions. The less polar fraction (0.18 g.) was crystallised from methanol to give 20,20-ethylenedioxy-2α-methyl-5α-pregnane-3,11-dione (0.13 g.), m.p. 179°–180°, $[\alpha]_D + 77.5°$.

The more polar fraction afforded 20,20-ethylenedioxy-3α-hydroxy-2α-methyl-5α-pregnan-11-one (0.39 g.) which on t.l.c. on silica using 1:1 ethyl acetate: petrol (b.p. 60°–80°) showed an $R_F$ of ca. 0.5 identical with that of a sample prepared as described in Example 25.

EXAMPLE 25

20,20-Ethylenedioxy-3α-hydroxy-2α-methyl-5α-pregnan-11-one

A solution of chloroiridic acid (10 mg.) and trimethyl phosphite (1.5 ml.) in aqueous 90% isopropanol (20 ml.) was heated under reflux for 17 hours. The solution was then neutralised with triethylamine, 20,20-ethylenedioxy-2β-methyl-5α-pregnane-3,11-dione (0.66 g.) was added, and the mixture was heated under reflux for 48 hr. The reaction mixture was cooled and partitioned between methylene chloride and water. The organic layer was dried (MgSO₄) and evaporated in vacuo. The residue (0.69 g.) was purified by preparative layer chromatography and crystallised from methyl acetate/petroleum ether (b.p. 60°–80°) to give 20,20-ethylenedioxy-3α-hydroxy-2α-methyl-5α-pregnan-11-one (0.42 g.), m.p. 167°–168°, $[\alpha]_D + 68°$.

EXAMPLE 26

3α-Hydroxy-2α-methyl-5α-pregnane-11,20-dione

A solution of 20,20-ethylenedioxy-3α-hydroxy-2α-methyl-5α-pregnane-11-one (0.38 g.) and toluene-p-sulphonic acid (30 mg.) in acetone (20 ml.) was kept at room temperature for 1½ hr. The reaction mixture was then evaporated to low bulk and an aqueous solution of sodium hydrogen carbonate was added. The precipitated solid (0.32 g.) was collected and purified by preparative t.l.c. and crystallised from methyl acetate/petrol (b.p. 60°–80°) to give the title compound (0.175 g.), m.p. 179°–180°, $[\alpha]_D + 125°$.

EXAMPLE 27

3α-Hydroxy-2α-methyl-5α-pregnane-11,20-dione

A solution of chloroiridic acid (40 mg.) and trimethyl phosphite (6 ml.) in aqueous 90% isopropanol (75 ml.) was heated under reflux for 17 hr. It was cooled and neutralised with triethylamine.

A portion of this reaction mixture (2 ml.) and 2α-methyl-5α-pregnane-3,11,20-trione (45 mg.) were heated together under reflux for 48 hr. The reaction mixture was then partitioned between water and methylene chloride. The organic layer was dried ($MgSO_4$) and evaporated to give title compound (20 mg.) with a nuclear magnetic resonance spectrum in $CDCl_3$) showing a doublet at $\tau$ 9.07 ($d$, J = 7Hz) for the 2$\alpha$-methyl protons and resembling that of the product of Example 26.

EXAMPLE 28

2$\alpha$-Bromo-3$\alpha$-hydroxy-5$\alpha$-pregnane-11,20-dione

A solution of chloroiridic acid (12 mg.) in aqueous 90% isopropanol (23 ml.) was treated with trimethyl phosphite (2 ml.), and the mixture was refluxed overnight. The solution was neutralized with triethylamine (3 ml.), then 2$\alpha$-bromo-5$\alpha$-pregnane-3,11,20-trione (419 mg.) was added, and the mixture refluxed for 3 hr.

The reaction mixture was poured into water and the product extracted with methylene chloride. The extract was washed with water, dried ($Na_2SO_4$), and evaporated in vacuo. The residue (301 mg.) was subjected to preparative t.l.c. The less polar fraction was the title compound (78 mg), with a nuclear magnetic resonance spectrum resembling that of the product from Example 12.

EXAMPLE 29

3$\alpha$-Hydroxy-16$\alpha$-methyl-5$\alpha$-pregnane-11,20-dione

To a stirred slurry of cuprous iodide (950 mg) in dry ether (75 ml) under dry nitrogen at 0° was added a solution of methyl-lithium in ether (1.6 M; 6 ml) until the initially formed yellow precipitate just redissolved to give a clear solution. To the stirred solution at 0° was added a solution of 3$\alpha$-hydroxy-5$\alpha$-pregn-16-ene-11,20-dione (600 mg) in dry tetrahydrofuran (50 ml). During the addition a bright yellow precipitate formed. The mixture was stirred at 0° for 30 minutes, and then poured into cold, saturated ammonium chloride solution (200 ml). More ether (200 ml) was added and the organic layer was separated, washed with saturated ammonium chloride solution (200 ml) and with water (200 ml) dried over sodium sulphate and purified by preparative t.l.c. in ethyl acetate to give a product which was further purified by preparative t.l.c. in ethyl acetate/chloroform, 1/1 to give a white solid (380 mg) which was recrystallised from ether/petrol to give title compound (248 mg) as colourless plates, m.p. 138°–140°, $[\alpha]_D$ + 99°, (c 0.95).

EXAMPLE 30 a.

2$\beta$-Bromo-3$\alpha$-(tetrahydropyran-2$\alpha$-yloxy)-5$\alpha$-pregnane-11,20-dione A solution of 2$\beta$-bromo-3$\alpha$-hydroxy-5$\alpha$-pregnane-11,20-dione (410 mg.), dihydropyran (1 ml.) and p-toluene sulphonic acid (8 mg.) in benzene (20 ml.) was stirred at room temperature for 20 minutes. The reaction mixture was diluted with ether, washed with aqueous 10% sodium bicarbonate and water, dried, filtered and evaporated to give a gum. Purification by preparative t.l.c. gave the title compound (495 mg.); $[\alpha]_D$ + 85°.

b. 3$\alpha$-Hydroxy-5$\alpha$-pregn-1-ene-11,20-dione

A mixture of 2$\beta$-bromo-3$\alpha$-(tetrahydropyran-2$\epsilon$-yloxy)-5$\alpha$-pregnane-11,20-dione (125 mg.), anhydrous lithium bromide (450 mg.) and calcium carbonate (350 mg.) in dimethylacetamide (3.5 ml.) was heated (100°–105°) for 4 hr. Further portions of anhydrous lithium bromide (400 mg.) and calcium carbonate (300 mg.) were added and heating continued for 2 hr. before cooling. Chloroform was added and the reaction mixture filtered to give a filtrate which was washed and then evaporated to dryness. The residual gum was dissolved in ethaol (5 ml.) and aqueous 2N-hydrochloric acid (ca. 0.2 ml.). After 4.5 hr. at room temperature the reaction mixture was diluted with chloroform, washed with aqueous 10% sodium bicarbonate and water, dried, filtered and evaporated to give an oil which, after purification by preparative t.l.c. afforded the pure title compound identical, as compared by t.l.c. and NMR, with the product in Example 12.

EXAMPLE 31

3$\alpha$,11$\alpha$-Dihydroxy-5$\alpha$-pregnan-20-one

A solution of 20,20-ethylenedioxy-3$\alpha$-hydroxy-5$\alpha$-pregnan-11-one (350 mg.) in mthanol (20 ml.) was treated with 25% aqueous acetic acid (2 ml.) at room temperature. After 18 hr. more 25 % aqueous acetic acid (2 ml.) was added and after a further 27 hr. the mixture was diluted with chloroform, washed with water, dried ($Na_2SO_4$) and evaporated to leave a white foam (300 mg.). Crystallisation from acetone and petroleum ether (b.p. 60°–80°) gave the title compound (160 mg.) as off-white rods; m.p. 152°–154°; $[\alpha]_D$ + 79°.

EXAMPLE 32

3$\alpha$-Hydroxy-17$\beta$-methoxycarbonyl-3$\beta$-methyl-5$\alpha$-androstan-11-one.

Bromine (0.54 ml.) was added to a solution of sodium hydroxide (1.5 g.) in water (13 ml.) at −5° over a period of 5 min. Cold dioxan (9 ml.) was then added and the resulting solution was added to a solution of 3$\alpha$-hydroxy-3$\beta$-methyl-5$\alpha$-pregnane-11,20-dione (1.0 g.) in dioxan (40 ml.) at 0°. The resulting mixture was kept at 5° for 1 hr., neutralised with concentrated hydrochloric acid and poured into water. Excess 2N-hydrochloric acid was then added and the precipitated solid was collected by filtration, dried in vacuo and dissolved in tetrahydrofuran (100 ml.). The resulting solution was treated with excess ethereal diazomethane at room temperature for 15 min. A few drops of acetic acid were then added and the mixture was partitioned between water and ether. The organic layer was washed with water, dried ($MgSO_4$) and evaporated. Recrystallisation of the residue gave the title compound (0.49 g., 45%) as white needles, m.p. 150°; $[\alpha]_D$ + 77° (c 1.0). (Found: C, 72.4; H, 9.2. $C_{23}H_{34}O_4$ requires C, 72.7; H, 9.4%)

EXAMPLE 33

3$\alpha$-Hydroxy-17$\beta$-methoxycarbonyl-5$\alpha$-androst-1-en-11-one.

A solution of 2$\beta$-bromo-3$\alpha$-hydroxy-17$\beta$-methoxycarbonyl-5$\alpha$-androstan-11-one. (3.48 g.,), dihydropyran (8 ml.) and p-toluenesulphonic acid (60 mg.) in benzene (150 ml.) was stirred at room temperature for 15 minutes before being washed with aqueous 10% sodium bicarbonate and water. The benzene solution was dried and evaporated to give a gum which was dissolved in dimethylacetamide (120 ml.). After the addition of anhydrous lithium bromide (14.4 g.) and calcium carbonate (11.2 g.) the mixture was heated (100°) for 6 hr. Cooling, dilution with chloroform and filtration gave a solution which was washed with water, dried, filtered and evaporated. The residue was dissolved in methanol (200 ml.) containing aqueous 2N hydrochloric acid (1 ml.). After 4 hr. the methanol was removed by evaporation and chloroform added. This solution, after being washed with aqueous 10% sodium bicarbonate and water, was dried, filtered and evaporated to an oil. The addition of ether resulted in crystallisation of the title compound (1.125 g.); m.p. 172°–175°; [α]$_D$ + 40°, (c 0.7).

EXAMPLE 34

3α-Hydroxy-17β-methoxycarbonyl-5α-androst-1-ene a. 2α, 3α-Epoxy-17β-methoxycarbonyl-5α-androstane A solution of 17β-methoxycarbonyl-5α-androst-2-ene (7.0 g.,) and 85% m-chloroperbenzoic acid (5.0 g.) in chloroform (125 ml.) was stirred for 1.5 hr. at room temperature and then diluted with chloroform (125 ml.). This solution was washed with aqueous 10% sodium bicarbonate and water prior to drying. Filtration and evaporation afforded a solid (8.075 g.) which was recrystallised from methylene chloride/cyclohexane to afford the pure title compound; [α]$_D$ + 67°, (c, 0.8).

b.
2β-Bromo-3α-hydroxy-17β-methoxycarbonyl-5α-androstane

Aqueous 48% hydrobromic acid (115 ml.) was added to a solution of the above epoxy compound (7.0 g.) in chloroform (350 ml.) and the mixture stirred at room temperature for 1 hr. The organic phase was separated, washed with aqueous 10% sodium bicarbonate and water and dried. Filtration and evaporation followed by crystallisation from methylene chloride/cyclohexane afforded the pure title compound (5.1 g.); [α]$_D$ + 72° (c, 0.6); m.p. 195°–198°.

c. A solution of the above bromo compound (4.0 g., 9.8 mmole), dihydropyran (10 ml.) and p-toluenesulphonic acid (80 mg) in benzene (200 ml.) was stirred at room temperature for 15 minutes. The reaction mixture was washed with aqueous 10% sodium bicarbonate and water prior to being dried and evaporated to afford the tetrahydropyranyl ether as a gum. The gum was dissolved in dry dimethylacetamide (150 ml.) to which was added anhydrous lithium bromide (18.0 g.) and calcium carbonate (14 g.). This mixture was heated (100°) for 6 hr. followed by cooling, dilution with chloroform and filtration. The chloroform solution was washed with water, dried, filtered and evaporated. The residue was dissolved in methanol containing aqueous 2N-hydrochloric acid (1 ml.). After 4 hr. at room temperature the methanol was removed by evaporation and chloroform added. This solution, after being washed with aqueous 10% sodium bicarbonate and water, was dried, filtered and evaporated to a gum which, after preparative t.l.c. and crystallisation from chloroform/petrol, yielded the pure title compound as white needles (480 mg.); m.p. 165°–168°; [α]$_D$ − 10.7°, (c, 0.7).

EXAMPLE A 0.04 g of 3α-hydroxy-5α-pregn-1-ene-11,20-dione were dissolved in 2 ml of acetone at 20°. The solutions was added to 1 g of Cremophor EL at 20° and stirred until homogeneous. The acetone was removed by a vigourous stream of nitrogen. The solution was diluted with sterile distilled water containing 0.0125 g of sodium chloride to give a final volume of 5 ml.

EXAMPLE B 0.02 g of 3α-hydroxy-5α-pregn-1-en-20-one were dissolved in 1 ml of acetone at 20°. The solution was added to 1 g of Cremophor EL at 20° and stirred until homogeneous. The acetone was removed by a vigorous stream of nitrogen. The solution was diluted with sterile distilled water containing 0.025 g of sodium chloride to give a final volume of 10 ml.

We claim:
1. A compound of the formula

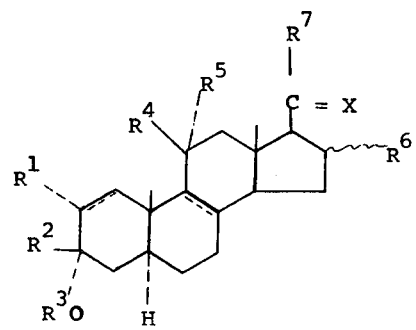

wherein $R^1$ is hydrogen or alkyl of 1–3 carbon atoms; $R^2$ is a hydrogen atom, methyl or ethyl; $R^3$ is a hydrogen or atom or tri (chloro or fluoro) acetyl; $R^4$ is a hydrogen atom, or epoxy linked to the 9 C atom; $R^5$ is a hydrogen atom; or $R^4$ and $R^5$ together represent an oxo group; $R^6$ is a hydrogen or halogen atom or methyl; $R^7$ is methyl or alkoxy of 1–6 carbon atoms; and X is an oxygen atom; the dotted lines at the 1(2) and 8(9) positions each indicating a single or double bond provided that there are not two double bonds at both of these positions in the same compound and provided that at least one of $R^1$, $R^2$ and $R^6$ is other than hydrogen when $R^4$ and $R^5$ are an oxo group or are both hydrogen and the 1(2) and 8(9) bonds are saturated and that $R^1$ is hydrogen when there is a 1(2) double bond.

2. A compound as claimed in claim 1 wherein $R^1$ is an alkyl group.
3. A compound as claimed in claim 1, wherein a double bond is present at the 1(2) position.
4. A compound as claimed in claim 1, wherein a single or double bond is present at the 8(9) position.
5. A compound as claimed in claim 1, wherein $R^6$ is a 16-α-chlorine atom.
6. A compound as claimed in claim 2, wherein $R^1$ is methyl.
7. Compounds as claimed in claim 1 wherein $R^4$ and $R^5$ together represent an oxo group.
8. Compounds as claimed in claim 1 wherein $R^7$ is a methyl group.
9. Compounds as claimed in claim 1 being:
3α-hydroxy-16β-methyl-5α-pregnane-11,20-dione;
16α-chloro-3α-hydroxy-5α-pregnane-11,20-dione;
9β,11β-epoxy-3α-hydroxy-5α-pregnane-20-one;
3α-hydroxy-3β-methyl-5α-pregnane-11,20-dione;
3α-hydroxy-2α-methyl-5α-pregnane-11,20-dione;
3α-hydroxy-5α-pregn-8-en-11,20-dione;
3α-hydroxy-5α-pregn-1-en-11,20-dione; or 3α-hydroxy-5α-pregn-1-en-20-one.

10. 3α-hydroxy-16α-methyl-5α-pregnane-11,20-dione or 3α-hydroxy-17-βmethoxycarbonyl-3β-methyl-5α-androstan-11-one.

11. 16α-Chloro3α-hydroxy-5α-pregnane-11,20-dione.

12. 3α-Hydroxy-2α-methyl-5α-pregnane-11,20-dione.

13. 3α-Hydroxy-5α-pregn-1-en-11,20-dione.

14. 3α-Hydroxy-5α-pregn-1-en-20-one.

* * * * *